United States Patent
Junio

(10) Patent No.: US 12,400,360 B2
(45) Date of Patent: Aug. 26, 2025

(54) SYSTEMS AND METHODS FOR SINGLE IMAGE REGISTRATION UPDATE

(71) Applicant: Mazor Robotics Ltd., Caesarea (IL)

(72) Inventor: Dany Junio, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 408 days.

(21) Appl. No.: 17/490,945

(22) Filed: Sep. 30, 2021

(65) Prior Publication Data

US 2022/0215578 A1 Jul. 7, 2022

Related U.S. Application Data

(60) Provisional application No. 63/134,850, filed on Jan. 7, 2021.

(51) Int. Cl.
*G06T 7/73* (2017.01)

(52) U.S. Cl.
CPC ...... *G06T 7/74* (2017.01); *G06T 2207/10121* (2013.01); *G06T 2207/30012* (2013.01); *G06T 2207/30204* (2013.01); *G06T 2207/30244* (2013.01)

(58) Field of Classification Search
None
See application file for complete search history.

(56) References Cited

U.S. PATENT DOCUMENTS

| | | | |
|---|---|---|---|
| 8,837,791 B2 | 9/2014 | Plakas et al. | |
| 9,066,751 B2 | 6/2015 | Sasso | |
| 9,101,395 B2 | 8/2015 | Gutierrez et al. | |
| 9,563,979 B2 | 2/2017 | Davey | |
| 9,710,880 B2 | 7/2017 | Xu et al. | |
| 9,713,506 B2 | 7/2017 | Fanson et al. | |
| 9,763,748 B2 * | 9/2017 | Hummelink | A61B 90/39 |
| 10,383,602 B2 | 8/2019 | Cho et al. | |
| 10,582,879 B2 | 3/2020 | Glossop | |
| 10,722,173 B2 | 7/2020 | Chen | |

(Continued)

FOREIGN PATENT DOCUMENTS

| | | |
|---|---|---|
| EP | 1659968 | 3/2012 |
| WO | WO 98/36371 | 8/1998 |

(Continued)

OTHER PUBLICATIONS

Windsor M, Peng J, Gupta A, Pivonka P, Milford MJ. Pose quality prediction for vision guided robotic shoulder arthroplasty. In2023 IEEE International Conference on Robotics and Automation (ICRA) May 29, 2023 (pp. 4797-4804). IEEE. (Year: 2023).*

(Continued)

*Primary Examiner* — Michelle M Entezari Hausmann
(74) *Attorney, Agent, or Firm* — Sheridan Ross P.C.

(57) ABSTRACT

A method including receiving information about a pose of each of a plurality of fiducials positioned on or within a patient; causing an imaging device to generate a single image of a portion of the patient, the single image depicting at least a portion of each of the plurality of fiducials; determining, based on the information and the single image, a pose of one or more anatomical elements represented in the single image; and comparing the determined pose of the one or more anatomical elements to a predetermined pose of the one or more anatomical elements.

17 Claims, 4 Drawing Sheets

(56) References Cited

U.S. PATENT DOCUMENTS

| | | | |
|---|---|---|---|
| 11,553,969 B1* | 1/2023 | Lang | G06T 7/0012 |
| 2003/0208122 A1* | 11/2003 | Melkent | A61B 90/11 |
| | | | 600/426 |
| 2008/0123927 A1* | 5/2008 | Miga | A61B 90/36 |
| | | | 382/131 |
| 2008/0161680 A1 | 7/2008 | von Jako et al. | |
| 2009/0088634 A1* | 4/2009 | Zhao | A61B 1/00193 |
| | | | 600/425 |
| 2011/0071389 A1* | 3/2011 | Simon | A61B 6/12 |
| | | | 600/426 |
| 2012/0053597 A1* | 3/2012 | Anvari | B25J 9/1689 |
| | | | 606/130 |
| 2012/0075285 A1* | 3/2012 | Oyagi | A63F 13/65 |
| | | | 345/419 |
| 2014/0187955 A1 | 7/2014 | Kang | |
| 2014/0272773 A1* | 9/2014 | Merritt | A61B 6/512 |
| | | | 433/29 |
| 2015/0313566 A1 | 11/2015 | Diers et al. | |
| 2017/0231715 A1 | 8/2017 | Roger et al. | |
| 2018/0092698 A1 | 4/2018 | Chopra et al. | |
| 2018/0200002 A1* | 7/2018 | Kostrzewski | G06T 7/344 |
| 2018/0256264 A1* | 9/2018 | McLachlin | A61B 5/0035 |
| 2019/0029561 A1 | 1/2019 | Kim et al. | |
| 2020/0098117 A1 | 3/2020 | Kask et al. | |
| 2020/0146754 A1 | 5/2020 | Row et al. | |
| 2020/0237444 A1 | 7/2020 | Snyder et al. | |
| 2021/0312949 A1* | 10/2021 | Chulev | G06Q 10/06398 |
| 2022/0087762 A1* | 3/2022 | Handa | A61B 34/37 |
| 2023/0115512 A1* | 4/2023 | Pasha | A61B 34/10 |
| | | | 345/419 |

FOREIGN PATENT DOCUMENTS

| | | |
|---|---|---|
| WO | WO 2012/103302 | 8/2012 |
| WO | WO 2013/038290 | 3/2013 |
| WO | WO 2020/163352 | 8/2020 |

OTHER PUBLICATIONS

Lee J, Kuo N, Deguet A, Dehghan E, Song DY, Burdette EC, Prince JL. Intraoperative 3D reconstruction of prostate brachytherapy implants with automatic pose correction. Physics in Medicine & Biology. Jul. 19, 2011;56(15):5011. (Year: 2011).*

Bowthorpe, Meaghan, and Mahdi Tavakoli. "Physiological organ motion prediction and compensation based on multirate, delayed, and unregistered measurements in robot-assisted surgery and therapy." IEEE/ASME Transactions on Mechatronics 21.2 (2015): 900-911. (Year: 2015).*

Extended Search Report for European Patent Application No. 21214406.7, dated Jun. 8, 2022, 11 pages.

* cited by examiner

SYSTEMS AND METHODS FOR SINGLE IMAGE REGISTRATION UPDATE

CROSS-REFERENCE TO RELATED APPLICATIONS

The present application claims the benefit of and priority, under 35 U.S.C. § 119(e), to U.S. Provisional Application Ser. No. 63/134,850, filed on Jan. 7, 2021, entitled "Systems and Methods for Single Image Registration Update," the entire disclosure of which is hereby incorporated herein by reference, in its entirety, for all that it teaches and for all purposes.

BACKGROUND

Images may be used in a surgical operation to perform registration. The images may be obtained prior to and/or during a surgical operation. The images may be taken throughout the surgical operation and may require use of an imaging device during the surgical operation.

SUMMARY

Example aspects of the present disclosure include:

A method according to at least one embodiment of the present disclosure comprises receiving information about a pose of each of a plurality of fiducials positioned on or within a patient; causing an imaging device to generate a single image of a portion of the patient, the single image depicting at least a portion of each of the plurality of fiducials; determining, based on the information and the image, a pose of one or more anatomical elements represented in the image; and comparing the determined pose of the one or more anatomical elements to a predetermined pose of the one or more anatomical elements.

Any of the aspects herein, further comprising updating a preexisting registration using the determined pose.

Any of the aspects herein, further comprising comparing the determined pose to a target pose of the one or more anatomical elements in a surgical plan.

Any of the aspects herein, further comprising determining a position of the imaging device relative to the plurality of fiducials based on use of a phantom.

Any of the aspects herein, wherein the plurality of fiducials comprises one or more screws.

Any of the aspects herein, wherein the plurality of fiducials comprises a plurality of different types of implants.

Any of the aspects herein, further comprising quantifying a change in pose of at least one of the one or more anatomical elements from the predetermined pose to the determined pose.

Any of the aspects herein, wherein the image further depicts a device held by a robot, and wherein the method further comprises locating the determined pose in a coordinate space corresponding to the robot based on the image.

Any of the aspects herein, wherein the information comprises a Computer Aided Design (CAD) model of at least one of the plurality of fiducials.

A system according to at least one embodiment of the present disclosure comprises a processor; and a memory storing instructions for execution by the processor that, when executed by the processor, cause the processor to receive information about a shape and a pose of a plurality of tracking devices disposed on or within a patient; cause an imaging device to generate a single image of a portion of the patient, the single image comprising at least a portion of each of the plurality of tracking devices; identify the portion of each of the plurality of tracking devices in the single image; calculate, based on the information and the identified portions of each of the plurality of tracking devices, a pose of one or more anatomical elements represented in the image; and quantify a difference between the calculated pose and the predetermined pose for at least one of the one or more anatomical elements.

Any of the aspects herein, wherein the imaging device is fixed in a first pose relative to the patient.

Any of the aspects herein, wherein a first surface of each of the portions of the plurality of tracking devices in the single image appears at an angle greater than ten degrees and less than eighty degrees relative to the imaging device.

Any of the aspects herein, wherein the single image is generated using fluoroscopy.

Any of the aspects herein, wherein the plurality of tracking devices comprises a plurality of different types of implants.

Any of the aspects herein, wherein at least one of the plurality of tracking devices is a screw implanted in the patient.

Any of the aspects herein, wherein the instructions further comprise instructions that cause the processor to compare the calculated pose of the one or more anatomical elements to a predetermined pose of the one or more anatomical elements.

Any of the aspects herein, wherein the plurality of tracking devices comprises one or more screws.

Any of the aspects herein, wherein each of the one or more anatomical elements is a vertebra.

A system according to at least one embodiment of the present disclosure comprises a processor; an imaging device; a plurality of fiducials disposed on or within a patient; and a memory storing instructions for execution by the processor that, when executed by the processor, cause the processor to receive information about a pose of the plurality of fiducials; cause the imaging device to generate an image of a portion of the patient, the image comprising the plurality of fiducials; determine, based on the information and the image, a pose of one or more anatomical tissues represented in the image; and cause the determined pose to be displayed on a user interface.

Any of the aspects herein, wherein the determined pose is displayed on the user interface as an overlay on a target pose.

Any aspect in combination with any one or more other aspects.

Any one or more of the features disclosed herein.

Any one or more of the features as substantially disclosed herein.

Any one or more of the features as substantially disclosed herein in combination with any one or more of the features as substantially disclosed herein.

Any one of the aspects/features/embodiments in combination with any one or more other aspects/features/embodiments.

Use of any one or more of the aspects or features as disclosed herein.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
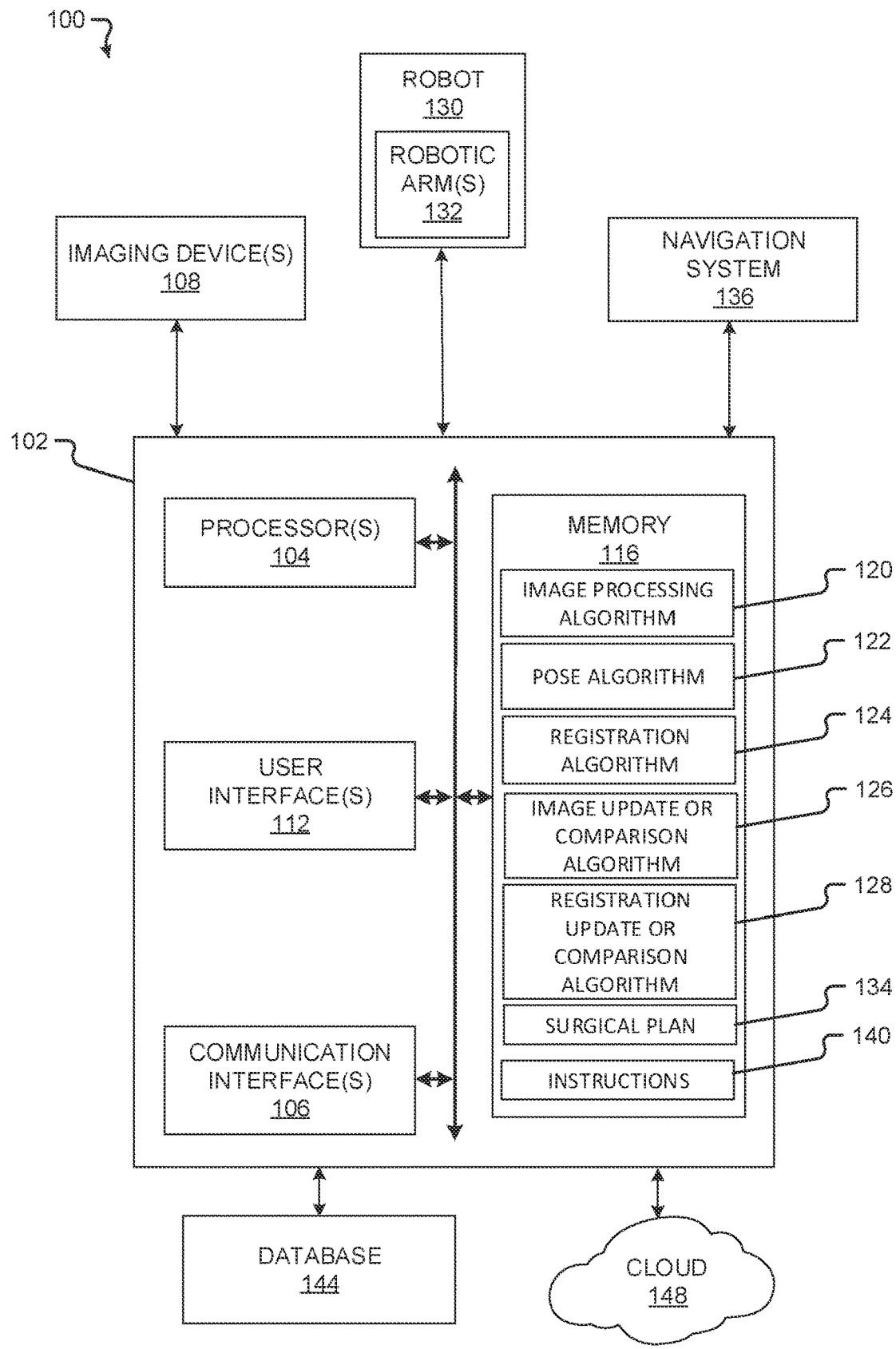
FIG. 1 illustrates a block diagram of a system in accordance with embodiments of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Registration of intraoperative fluoroscopy to a pre-operative Computed Tomography (CT) scan generally involves taking two fluoroscopic images. Each image exposes the patient—and possibly one or more attending medical personnel—to ionizing radiation, which is known to be harmful. Additionally, capturing two fluoroscopic images may be time consuming, and may create additional room for error, as the amount of error grows as the number of captured images grows. Surgeons may benefit from a reduced number of actions and execution time associated with capturing two images, while patients may benefit from reduced anesthesia time.

According to embodiments of the present disclosure, fiducial markers with known item size are captured in an image. The fiducial markers may include any surgical accessories of known size and reflectivity. Embodiments of the present disclosure further include taking (e.g., capturing) a single, relevantly angled C-arm shot of the fiducial markers. In other words, the C-arm shot is angled such that the fiducial markers may be used to represent a missing depth indication. Embodiments of the present disclosure may be used to update an existing, previously taken registration or to create a new registration.

Embodiments of the present disclosure beneficially enable generating or updating a registration using only a single image. Embodiments of the present disclosure also reduce the amount of work required to capture additional images for registration, while also reducing the amount of radiation the patient experiences during a surgery or surgical procedure. Embodiments of the present disclosure also beneficially enable improved registration accuracy during surgeries or surgical procedures involving a robot and/or robotic arms.

Turning first to FIG. 1, a block diagram of a system 100 according to at least one embodiment of the present disclosure is shown. The system 100 may be used, for example, to obtain and process image data; execute one or more methods described herein; execute one or algorithms described herein; and/or facilitate a surgery or surgical procedure. The system 100 comprises a computing device 102, one or more imaging devices 108, a robot 130, a navigation system 136, a database 144, and a cloud or other network 148. Notwithstanding the foregoing, systems according to other embodiments of the present disclosure may omit one or more components of the system 100. For example, in some embodiments, the system 100 may omit one or more components of the computing device 102. Additionally, systems according to other embodiments of the present disclosure may arrange one or more components of the system 100 differently (e.g., the imaging device 108, the robot 130 and/or components thereof, and/or the navigation system 136 may comprise one or more of the components of the computing device 102, and/or vice versa), and/or include additional components not shown.

The computing device 102 comprises at least one processor 104, at least one communication interface 106, at least one user interface 112, and at least one memory 116. A computing device according to other embodiments of the present disclosure may omit one or both of the communication interface(s) 106 and/or the user interface(s) 112.

The at least one processor 104 of the computing device 102 may be any processor identified or described herein or any similar processor. The at least one processor 104 may be configured to execute instructions 140 stored in the at least one memory 116, which instructions 140 may cause the at least one processor 104 to carry out one or more computing steps utilizing or based on data received, for example, from the imaging device 108, the memory 116, the robotic arm 130 and/or components thereof, the navigation system 136, the database 144, and/or the cloud 148. The instructions 140 may also cause the at least one processor 104 to utilize one or more algorithms stored in the memory 116. In some embodiments, the at least one processor 104 may be used to control the one or more imaging devices 108, the robot 130 and/or components thereof (e.g., one or more robotic arms 132), and/or the navigation system 136 during a surgical procedure, including during an imaging procedure or other procedure being carried out autonomously or semi-autonomously by the robot 130 using the navigation system 136.

The computing device 102 may also comprise the at least one communication interface 106. The at least one communication interface 106 may be used for receiving sensor data (e.g., from the one or more imaging devices 108, the robot 130 and/or the navigation system 136), a surgical plan (e.g., a surgical plan 134) or other planning data, or other information from an external source (such as the database 144, the cloud 148, and/or a portable storage medium (e.g., a USB drive, a DVD, a CD)), and/or for transmitting instructions, images, or other information from the at least one processor 104 and/or the computing device 102 more generally to an external system or device (e.g., another computing device 102, the one or more imaging devices 108, the robot 130, the navigation system 136, the database 144, the cloud 148, and/or a portable storage medium (e.g., a USB drive, a DVD, a CD)). The at least one communication interface 106 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 106 may be useful for enabling the device 102 to communicate with one or more other processors 104 or computing devices 102, whether to reduce the time needed to accomplish a computing-intensive task or for any other reason.

The at least one user interface 112 may be or comprise a keyboard, mouse, trackball, monitor, television, touchscreen, button, joystick, switch, lever, and/or any other device for receiving information from a user and/or for providing information to a user of the computing device 102. The at least one user interface 112 may be used, for example, to receive a user selection or other user input in connection with any step of any method described herein; to receive a user selection or other user input regarding one or more configurable settings of the computing device 102, the one or more imaging devices 108, the robot 130, the navigation system 136, and/or any other component of the system 100; to receive a user selection or other user input regarding how and/or where to store and/or transfer data received, modified, and/or generated by the computing device 102; and/or to display information (e.g., text, images) and/or play a sound to a user based on data received, modified, and/or generated by the computing device 102. Notwithstanding the inclusion of the at least one user interface 112 in the system 100, the system 100 may automatically (e.g., without any input via the at least one user interface 112 or otherwise) carry out one or more, or all, of the steps of any method described herein.

Although the at least one user interface 112 is shown as part of the computing device 102, in some embodiments, the computing device 102 may utilize a user interface 112 that is housed separately from one or more remaining components of the computing device 102. In some embodiments, the user interface 112 may be located proximate one or more other components of the computing device 102, while in other embodiments, the user interface 112 may be located remotely from one or more other components of the computer device 102.

The at least one memory 116 may be or comprise RAM, DRAM, SDRAM, other solid-state memory, any memory described herein, or any other tangible non-transitory memory for storing computer-readable data and/or instructions. The at least one memory 116 may store information or data useful for completing, for example, any step of a method 200, 300, and/or 400 described herein. The at least one memory 116 may store, for example, instructions 140, and/or one or more algorithms. In some embodiments, the memory 116 may also store one or more preoperative and/or other surgical plans (e.g., surgical plan 134); one or more images of one or more patients, including in particular of an anatomical feature/element of the one or more patients on which one or more surgical procedures is/are to be performed; images and/or other data received from the one or more imaging devices 108 (or either one of the foregoing), the robot 130, and/or the navigation system 136 (including any component thereof) or elsewhere; and/or other information useful in connection with the present disclosure.

The instructions 140, as described above, may be or comprise any instructions for execution by the at least one processor 104 that cause the at least one processor to carry out one or more steps of any of the methods described herein. The instructions 140 may be or comprise instructions for determining a pose of one or more anatomical elements (e.g., one or more vertebra) and/or a plurality of fiducials (e.g., tracking markers); instructions for comparing a determined pose of one or more anatomical elements against a predetermined pose of one or more anatomical elements; instructions for quantifying a difference between the determined pose and the predetermined pose of the one or more anatomical elements; instructions for locating the determined pose in a coordinate space; instructions for registering an image space to a patient space; instructions for manipulating a robot and/or a robotic arm such as the robot 130 and/or one or more robotic arms 132 to carry out any one or more of the methods described herein; or otherwise. The instructions 140 may additionally or alternatively enable the at least one processor 104, and/or the computing device 102 more generally, to operate as a machine learning engine that receives data and outputs one or more thresholds, criteria, algorithms, and/or other parameters that can be utilized during an interbody implant insertion procedure, and/or during any other surgical procedure in which information obtained from an interbody tool as described herein may be relevant, to increase the likelihood of a positive procedural outcome.

The one or more algorithms previously mentioned may be or comprise any algorithms useful for converting sensor data received from sensors (including imaging sensors of the one or more imaging devices 108) and/or from gauges into meaningful information (e.g., registering an image space into a patient space, spatial position information relative to a given coordinate system, a calculated force value, a pressure value, a distance measurement). The one or more algorithms may further be or comprise one or more image processing algorithms 120, one or more pose algorithms 122, one or more registration algorithms 124, one or more image update or comparison algorithms 126, and one or more registration update or comparison algorithms 128. The one or more algorithms may be useful for controlling the one or more imaging devices 108, the robot 130, and/or the navigation system 136. The one or more algorithms may further be or comprise algorithms useful for generating one or more recommendations to a surgeon or other user of the system 100 based on information received from a sensor and/or a gauge, and/or for modifying a preoperative or other surgical plan (e.g., a surgical plan 134) based on such information and/or an evaluation of such information. In some embodiments, the one or more algorithms may be or include machine learning algorithms useful for analyzing historical data (e.g., stored in a database 144).

The database 144 may store any information described herein as being stored in the memory 116, including instructions such as the instructions 140 and/or algorithms such as the one or more algorithms (e.g., one or more pose algorithms 122, etc.). In some embodiments, the database 144 stores one or more preoperative or other surgical plans (e.g., a surgical plan 134). The database 144 may additionally or alternatively store, for example, information about or corresponding to one or more characteristics of one or more of the one or more imaging devices 108, the robot 130, and the navigation system 136; and/or other information regarding available tools and/or equipment for use in connection with a surgical procedure. The database 144 may be configured to provide any such information to the one or more imaging devices 108, the robot 130, the computing device 102, the navigation system 136, or to any other device of the system 100 or external to the system 100, whether directly or via the cloud 148. In some embodiments, the database 144 may be or comprise part of a hospital image storage system, such as a picture archiving and communication system (PACS), a health information system (HIS), and/or another system for collecting, storing, managing, and/or transmitting electronic medical records including image data. Also in some embodiments, the memory 116 may store any of the information described above.

The cloud 148 may be or represent the Internet or any other wide area network. The computing device 102 may be connected to the cloud 148 via the communication interface 106, using a wired connection, a wireless connection, or both. In some embodiments, the computing device 102 may communicate with the database 144 and/or an external device (e.g., a computing device) via the cloud 148.

The navigation system 136 may provide navigation for a surgeon and/or for the robot 130 and/or components thereof (e.g., one or more robotic arms 132) during an operation or surgical procedure. The navigation system 136 may be any now-known or future-developed navigation system, including, for example, the Medtronic StealthStation™ S8 surgical navigation system. The navigation system 136 may include a camera or other sensor(s) for detecting and/or tracking one or more reference markers, navigated trackers, or other objects within an operating room or other room where a surgical procedure takes place. In some embodiments, the navigation system 136 may comprise a plurality of sensors. In various embodiments, the navigation system 136 may be used to track a position of the one or more imaging devices 108, of the robot 130, and/or of one or more other objects to which the navigation system 136 has a line of sight (where the navigation system is an optical system) or that are otherwise detectable by the navigation system 136. The navigation system 136 may be used to track a position of one or more reference markers or arrays or other structures useful for detection by a camera or other sensor of the navigation system 136. The navigation system 136 may include a display for displaying one or more images from an external source (e.g., the computing device 102, the cloud 148, or other source) or a video stream from the navigation camera, or from the one or more imaging devices 108, or from another sensor. In some embodiments, the system 100 may operate without the use of the navigation system 136.

The imaging device 108 is configured to capture, store, and/or transmit images and/or image data (e.g., image metadata, pixel data, etc.) between various components of the system 100 (e.g., to the robot 130, the navigation system 136, the computing device 102, any combination thereof, etc.). The imaging device 108 may comprise one or more sensors, which may assist the system 100 in determining the position and orientation (e.g., pose) of the imaging device 108. In some embodiments, the system 100 may determine the position and orientation of the imaging device 108 relative to one or more other components (e.g., the robot 130) in the system 100. The determination of the position and orientation of the imaging device 108 may assist the system 100 when processing data related images captured by the imaging device 108. In various examples, the image data captured by the imaging device 108 may comprise data corresponding to an anatomical feature of a patient, or to a portion thereof. The imaging device 108 may be or comprise, for example, an ultrasound scanner, an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography scanner, a thermographic camera (e.g., an infrared camera), or any other imaging device capable of obtaining images of an anatomical feature of a patient. In some embodiments, the imaging device 108 may comprise additional or alternative connective components (e.g., a phantom) which may facilitate the capture and/or processing of images captured by the imaging device 108. The connective components may filter and/or process the light received that is not orthogonal to the imaging device 108 (e.g., sides and/or borders of images associated with non-flat images) to provide image data consistent with a flat image (e.g., all parts of the image are orthogonal to the imaging device 108).

In some embodiments, one or more images captured by the imaging device 108 may be used to verify a registration (e.g., a transformation of different sets of data, such as the data associated with the captured images, into a single coordinate system, or a correlation of one coordinate system or space to another coordinate system or space) for a surgery or surgical procedure. For example, the surgery or surgical procedure may comprise registering a coordinate system of a robot and/or robotic arm (e.g., a robotic arm 132), to a coordinate system of a patient. In some embodiments, a coordinate system or space of a navigation system may additionally or alternatively be registered to a robotic coordinate system and/or to a patient coordinate system. The registration may thereafter enable the robot to be moved to specific locations relative to the patient. However, if a position of one or more of the patient, the robot, and/or the navigation system changes relative to any other one or more of the patient, the robot, and/or the navigation system, then the registration may become invalid. Images from the imaging device 108 may therefore be used to determine whether the registered entities are or are not still in the same position relative to each other.

Images captured by the imaging device 108 may also be used to update a registration or to perform an additional registration, whether because the patient moved relative to the robot or vice versa or for any other reason. The system 100 and/or components thereof (e.g., a computing device 102) may then use the updated or additional registration going forward.

The robot 130 may be any surgical robot or surgical robotic system. The robot 130 may be or comprise, for example, the Mazor X™ Stealth Edition robotic guidance system. The robot 130 may comprise one or more robotic arms 132. The robotic arm 132 may, in some embodiments, assist with a surgical procedure (e.g., by holding a tool in a desired trajectory or pose, by supporting the weight of a tool while a surgeon or other user operates the tool, by moving a tool to a particular pose under control of the surgeon or other user, and/or otherwise) and/or automatically carry out a surgical procedure.

The robotic arm 132 may have one, two, three, four, five, six, seven, or more degrees of freedom. The robotic arm 132 may comprise one or more segments. Each segment may be secured to at least one adjacent member by a joint, such that the robotic arm 132 is articulated. The joint(s) may be any type of joint that enables selective movement of the member relative to the structure to which the joint is attached (e.g., another segment of the robotic arm). For example, the joint may be a pivot joint, a hinge joint, a saddle joint, or a ball-and-socket joint. The joint may allow movement of the member in one dimension or in multiple dimensions, and/or along one axis or along multiple axes. While a proximal end of the robotic arm 132 may be secured to a base (whether via a joint or otherwise), a distal end of the robotic arm 132 may support an end effector. The end effector may be, for example, a tool (e.g., a drill, saw, imaging device) or a tool guide (e.g., for guiding a biopsy needle, ablation probe, or other tool along a desired trajectory).

The robotic arm 132 may comprise one or more pose sensors. The pose sensors may be configured to detect a pose of the robotic arm or portion thereof, and may be or comprise one or more rotary encoders, linear encoders, incremental encoders, or other sensors. Data from the pose sensors may be provided to a processor of the robotic arm 132, to a processor 104 of the computing device 102, and/or to the navigation system 136. The data may be used to calculate a position in space of the robotic arm 132 relative to a predetermined coordinate system. Such a calculated position may be used, for example, to determine a position in space of one or more of the plurality of sensors that are attached to the robotic arm 132. Additionally and/or alternatively, one or more tracking markers may be affixed or otherwise attached to the robotic arm 132, and the navigation system 136 may utilize the one or more tracking markers to determine a position in space (e.g., relative to a navigation coordinate system) of the robotic arm 132 and/or of an end effector supported thereby.

Embodiments of the present disclosure may comprise systems 100 with more than one robotic arm 132. For example, one or more robotic arms may be used to support the imaging device 108. As another example, multiple robotic arms may be used to hold different tools or medical devices, each of which may need to be used simultaneously to successfully complete a surgical procedure. For example, in some embodiments the robot 130 and/or one or more of the robotic arms 132 may hold a device (e.g., a tracking device, a fiducial, etc.) at a fixed location relative to the robot 130 and/or a patient. An image of the held device may be captured by the imaging device 108, which image may be used by one or more components of the system 100 (e.g., a processor 104) to determine a pose in a coordinate space. For instance, during registration, the system 100 may utilize the captured image and the device displayed therein to register the image space (e.g., the coordinates of the image) to the coordinate space (e.g., the space in which the device is being held). Additionally or alternatively, the system 100 may determine the pose of the device, which may be used for registration or for defining a coordinate space.

Figure 2:
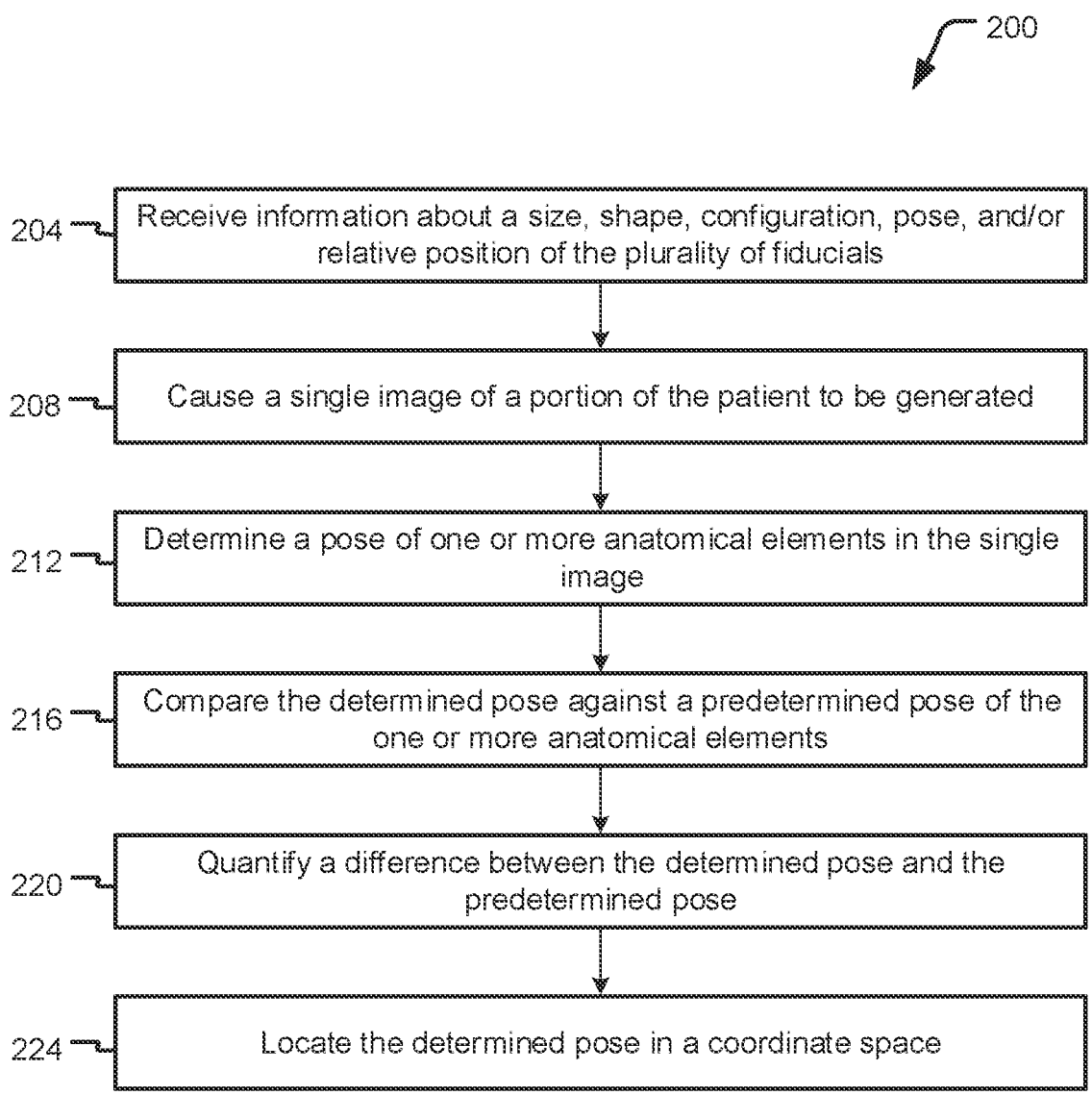
FIG. 2 shows a flowchart of a method in accordance with embodiments of the present disclosure.

Turning now to FIG. 2, a method 200 for a single image pose determination of one or more anatomical elements according to embodiments of the present disclosure is shown. The method 200 may be executed in part or in whole, for example, by a computing device 102 or similar device, and may utilize a system 100 and/or one or more components thereof (e.g., a processor 104, one or more imaging devices 108, a navigation system 136, and/or combinations thereof, etc.). The at least one processor used to carry out the method 200 and/or one or more steps thereof may be the same as or similar to the processor(s) 104 of the computing device 102 described above. The at least one processor may be part of a robot (such as a robot 130 comprising one or more robotic arms 132) or part of a navigation system (e.g., a navigation system 136). A processor other than any processor described herein may also be used to execute the method 200. The at least one processor may perform the method 200 by executing instructions (such as the instructions 140) stored in a memory (such as the memory 116). One or more aspects of the method 200 may be performed by or with a robot and/or surgical robotic arm (e.g., a robotic arm 132 attached to a robot 130) and/or components thereof. The method 200 may be used, for example, to update a registration based on movement of a patient and/or one or more components of the system 100 during, for example, a surgery or surgical procedure. For instance, the patient may have shifted during surgery, and a new registration may be required.

The method 200 comprises receiving information about a size, shape, configuration, pose, and/or relative position of each of a plurality of fiducials (step 204). The plurality of fiducials may be positioned on or within the patient. The plurality of fiducials may be or comprise one or more screws, rods, intervertebral bodies, or other medical devices implanted into a patient. The information may be received via a user interface such as a user interface 112 and/or a communication interface (e.g., communication interface 106) and may be stored by a computing device (e.g., a computing device 102) in a memory (e.g., a memory 116). In some embodiments, the information may be received from one or more components of a system 100, such as from a database 144 and/or a cloud 148 and/or from external components of the system 100 (e.g., from other computing devices and/or databases). The information may comprise a CAD (computer-aided design) model of one or more of the plurality of fiducials. The information may correspond to a reflectivity of the one or more fiducials. The information may correspond to a surgical plan and/or to data from a robot used to execute a surgical plan, and may include, for example, information about a pose (e.g., a position and orientation), or a position or an orientation, of a given fiducial as inserted into the patient relative to the patient's anatomy. The information may comprise additional data about the plurality of fiducials (e.g., number of the fiducials inserted into the patient, relative time of placement of the plurality of fiducials, etc.) and/or the surgical procedure (e.g., type of surgical procedure, duration of surgical procedure, etc.).

The information received may depict at least a size, shape, configuration, pose, and/or relative position of the fiducials. The size of each of the plurality of fiducials may be or comprise the dimensions (e.g., length, width, height, etc.) of each fiducial. The shape of each of the plurality of fiducials may be information directed to an outline, geometric form, contours, surfaces, edges, and/or the like of the plurality of fiducials. The pose of each of the plurality of fiducials may be the location and orientation of each of the fiducials relative to the patient or in another specified coordinate space. The relative position of each fiducial may be a measurement of the relative distance of each fiducial from the remaining fiducials of the plurality of fiducials. The information may, in some embodiments, be input into one or more algorithms (e.g., a pose algorithm 122) to extract or determine additional information therefrom and/or to transform the information into information that is useful for the system (e.g., information useful for or relating to registration). In some embodiments, the information about the plurality of fiducials may be further stored/saved (e.g., in a database 144, a memory 116, or elsewhere) within the system 100.

The method 200 also comprises causing a single image of a portion of the patient to be generated (step 208). For instance, a computing device 102 (and more specifically, a processor 104) may cause an imaging device (e.g., an imaging device 108) to generate (e.g., capture) an image of a portion of the patient that comprises on or more of the plurality of fiducials. The single image may be, for example, a fluoroscopy image. In some embodiments, the processor may cause the imaging device to move into a first pose (e.g., position and orientation) relative to the patient, such that the imaging device can view every fiducial of the plurality of fiducials. In some embodiments, the first pose may be a position and orientation such that every fiducial of the plurality of fiducials is seen by the imaging device and such that relative spacing and depth information (e.g., where each fiducial is located in a coordinate system and how far away each fiducial is from the camera with respect to the coordinate system) of each of the plurality of fiducials may be determined from the captured image and the information received in the step 204. In some embodiments, only portions of each of the plurality of fiducials may be captured by the image. For instance, only a percentage of each of the plurality of fiducials (e.g., 1%, 2%, 5%, 10%, 15%, 25%, 50%, 75%, 80%, 90%, etc.) may be present in the image. In such embodiments, the percentage may be different for each of the plurality of fiducials. In some embodiments, the image may only depict a percentage of the total number of fiducials (e.g., only half of the total number of fiducials). In some embodiments, the method 200 causes only a single image of the portion of the patient to be generated. The imaging device may send the captured image to one or more components in the system 100 (e.g., to the computing device 102, the database 144, etc.) and/or to components outside the system 100. Each of the fiducials of the plurality of fiducials may be present in the image and may be distinguishable from other artifacts or structure in the image. For instance, in embodiments where the plurality of fiducials comprises screws, the imaging device 108 may emit radioactive waves (e.g., X-rays) with a detector positioned such that the plurality of fiducials is between the imaging device 108 and the detector. The resulting image may highlight (e.g., display in a different color, texture, intensity, and/or shape) the plurality of fiducials positioned within the patient. As previously noted, the plurality of fiducials may be attached or located proximate to one or more anatomical elements (e.g., internal organs, bones, ligaments, tendons, muscle structures, other soft tissues and/or hard tissues, etc.). In such embodiments, the capture of the image depicting the portion of the patient may also depict relative positions of the one or more anatomical elements to which the fiducials are attached or proximally located.

In some embodiments, one or more of the plurality of fiducials may be placed on or within the patient before a surgery or surgical procedure. For instance, one or more of the plurality of fiducials may be fixed to the skin of the patient (or even to the bony anatomy of the patient, whether via a small incision or otherwise) before a surgery begins. Also in some embodiments, one or more of the plurality of fiducials may have been previously implanted in a patient (e.g., during an initial surgery), permitting the system 100 to capture (e.g., via an imaging device 108) a relative layout of the plurality of fiducials prior to a subsequent surgery (e.g., a revision surgery). The system 100 may use the captured information intraoperatively, to compare the layout of the plurality of fiducials with a new image of the plurality of fiducials captured during or after the surgery or surgical procedure.

Also, as noted above, in some embodiments, the one or more of the plurality of fiducials may be implanted in the patient. For instance, the surgery or surgical procedure may be directed toward procedures performed within the patient. In such embodiments, one or more of the plurality of fiducials may be implanted in specific locations in the patient (e.g., anatomical features, structure, or the like). This may permit the system 100 and/or components thereof to determine the relative anatomical structure of the patient. The plurality of fiducials may then be removed from the patient during and/or after the surgery or surgical procedure. The plurality of fiducials is in no way limiting, and examples may include screws, tracking devices, radio frequency identification (RFID) tags, or the like. The screws may be, for example, pedicle screws, cortical screws, cancellous screws, combinations thereof, and/or the like.

In some embodiments, the plurality of fiducials may be positioned such that a depth measurement may be obtained from the image. The depth measurement may be determined based on the viewing a first surface of a fiducial. For instance, the first surface of the fiducial may be angled relative to the first pose of the imaging device, such that the imaging device may only see an isometric (e.g., perspective) view of the fiducial. In other words, the fiducial is neither orthogonal (e.g., such that the imaging device views only a top or bottom of the fiducial without viewing a side) nor lateral (e.g., such that the imaging device views only a side of the fiducial without viewing the top or bottom). Rather, the view of the fiducial seen by the imaging device (and subsequently appearing in the image) may be such that the first surface is viewed in addition to at least one of the top, bottom, and side of the fiducial. The appearance of at least two surfaces may permit the method 200 to determine a depth of the fiducial (e.g., how far away each point of the fiducial is from the imaging device with respect to a coordinate system) using the information received in the step 204 and by determining an angle of the fiducial in the captured image.

The method 200 also comprises determining a pose of one or more anatomical elements in the single captured image (step 212). The determining may be based on the information received in the step 204 as well as the image generated in the step 208. The determining may use one or more algorithms such as a pose algorithm 122. The pose determination may include using coordinates for and/or an orientation of the plurality of fiducials attached to or near the one or more anatomical elements. In some embodiments, the pose algorithm may be configured to calculate the one or more poses based on the plurality of fiducials captured in the image and the information received in the step 204. For instance, the pose algorithm may determine that a fiducial is attached to or near an anatomical element, and may use the received information about the size, shape, configuration, pose, and/or relative position of the fiducial, together with the image generated in the step 208, to define a pose of the anatomical element. In some embodiments, the pose algorithm may output the defined pose relative to a predetermined coordinate system, a robot, and/or other components (e.g., other components of the system 100). In some embodiments, the pose algorithm may be, use, or be used by artificial intelligence (AI), machine learning (e.g., deep learning), and/or other solutions to identify, detect, or otherwise recognize the fiducials and/or determine a pose of the anatomical element. The determined pose may be sent to and/or stored in one or more components of the system 100. The method 200 may additionally or alternatively make use of an image processing algorithm (e.g., an image processing algorithm 120). The image processing algorithm may receive the captured image (e.g., from the imaging device) and may filter, process, or otherwise digitally manipulate the single image. Such post-image processing may improve storage efficiency of the image and/or may improve the image quality to more easily facilitate the pose determination (e.g., by improving the quality of the image passed to the pose algorithm).

In some embodiments, the depth of each of the plurality of fiducials may be determined. In embodiments where the imaging device captures a view of at least two surfaces of the fiducial, the relative depth may be determined through an angle measurement together with the information received in the step 204. For instance, the pose algorithm may determine a relative angle of the fiducial in the image of the portion of the patient and may calculate the pose of the fiducial using the angle and position information (e.g., information received about the relative position of the fiducials). A first surface of each fiducial may be the surface from which the pose algorithm measures the relative angle. The selection of the first surface is not limited, and the choice of the first surface may be arbitrary and may additionally or alternatively be selected based on the appearance of the fiducial in the image, based on predetermined instructions for the designation of the first surface, and/or the like. The angle of the first surface may appear in the single image at an angle of greater than 0 degrees and less than 90 degrees, greater than 10 degrees and less than 80 degrees, greater than 20 degrees and less than 70 degrees, etc. It is to be understood, however, that the above degree ranges are in no way limiting to the embodiments of the present disclosure, and additional or alternative angle ranges of between 0 and 90 degrees are possible. The method 200 may use the determined fiducial location to further determine the pose of one or more anatomical elements. For instance, in embodiments where the plurality of fiducials have been affixed to one or more anatomical elements, the pose of the fiducial may allow the processor to determine the relative pose of the one or more anatomical elements. In some embodiments, one or more of the plurality of fiducials may be attached on or near the one or more anatomical elements, which may allow for the determination of the pose of the one or more anatomical elements based on the relative poses of the plurality of fiducials and the known distances between the plurality of fiducials and the one or more anatomical elements. In some embodiments, the pose of one or more anatomical elements is compared to a target pose. For instance, the target pose may be a predicted or expected pose of each of the one or more anatomical elements. The comparison algorithm may compare the determined pose against the target pose to determine a level of accuracy (e.g., how closely the determined pose is to a desired pose). In some embodiments, the method may include sending a warning to a user interface (e.g., a user interface 112) when the determined pose is outside a threshold accuracy level from the target pose.

The method 200 also comprises comparing a determined pose of one or more anatomical elements with a predetermined pose of the one or more anatomical elements (step 216). The predetermined pose of the one or more anatomical elements may correspond to a previous registration, and/or may be provided by, for example, one or more components of the system 100. In some embodiments, the predetermined pose may have been determined before a surgery or surgical procedure has taken place. For instance, the predetermined pose may comprise information (e.g., coordinates, images, combinations thereof, etc.) about where the one or more anatomical elements and/or the plurality of fiducials should be or were located based on previously captured data (e.g., an image of the one or more anatomical elements and/or the plurality of fiducials taken before the surgery or surgical procedure, or during a previous registration). The predetermined pose may correspond to a preoperative CT or MRI image. The method 200 may implement a comparison algorithm (e.g., an image update or comparison algorithm 126) to compare the determined pose of the one or more anatomical elements to a predetermined pose determined at an earlier time. In some embodiments, the comparison algorithm may take into account a change in position of the patient from a first position in which the predetermined pose was determined and a second position in which the determined pose may be calculated. For example, the predetermined pose may have been determined when the patient was in a supine position, and the determined pose may be based on the patient being in the prone position. The comparison algorithm may compare the determined pose to the predetermined pose based in part on this switch in patient position.

The method 200 also comprises quantifying a difference between a determined pose of one or more anatomical elements and a predetermined pose of the one or more anatomical elements (step 220). The quantifying may make use of one or more algorithms (e.g., an image update or comparison algorithm 126) to provide a quantity reflecting the difference between the determined pose and the predetermined pose. For instance, the algorithm may receive the results of the comparison of the relative positions of the one or more anatomical elements in the determined pose to the one or more anatomical elements in the predetermined pose and may base the quantification on the compared positions. The quantified difference may be percent-based (e.g., 0.1% different, 0.2% different, 1% different, 5% difference, 10% difference, etc.). In some embodiments, the percent-based difference may be based on the percentage of the determined pose that matches (e.g., overlaps, lines up with, etc.) the predetermined pose. The percent-based difference may use weighted averages if reporting the percent-based difference for all the anatomical elements and may additionally or alternatively report percent-based differences for each anatomical element of the one or more anatomical elements. In some embodiments, a 100% difference may indicate that the determined pose has no pose overlap with the predetermined pose. In some embodiments, the quantified difference may be a positional or angular difference (e.g., 0.1 mm difference, 0.2 mm difference, 1 mm difference, 0.1 degree difference, 0.2 degree difference, 1 degree difference, etc.). The positional difference may be based on the relative coordinate change of the determined pose from the predetermined pose in one or more directions (e.g., positional changes along the length, width, and/or height of the one or more anatomical elements). In some embodiments, the algorithm may base the positional difference on the captured image of the one or more anatomical elements. For example, the algorithm may receive a captured image of the one or more anatomical elements before the start of a surgery or surgical procedure, which may be designated as the predetermined pose. Such an image may be, for example, a CT scan, an MRI image, or another preoperative image. The image may be two-dimensional or three-dimensional. The algorithm may additionally receive the single image captured by the imaging device, which may indicate the determined pose. The single image may be, for example, a fluoroscopy image or an ultrasound image. The single image may be two-dimensional, but third dimension information may be inferred and/or calculated therein using aspects of the present disclosure (including, e.g., by calculating depth information using the imaged fiducials). The algorithm may compare the two images of the one or more anatomical elements and determine a percentage or positional change from the predetermined pose to the determined pose.

The method 200 also includes locating the determined pose in a coordinate system (step 224). The method 200 may make use of one or more algorithms (e.g., a pose algorithm 122) in locating the determined pose in a coordinate system. For instance, the algorithm may receive the determined pose of the one or more anatomical elements in the single image and may map the pose to a coordinate system in a coordinate space. In some embodiments, the coordinate space may be similar to, or the same as, a patient space. The mapping may be based on the position of the imaging device (e.g., an imaging device 108) when the image was captured and may additionally or alternatively be based on the positioning of the plurality of fiducials relative to the one or more anatomical elements. The pose of each of the one or more anatomical elements in the coordinate space may be stored/saved (e.g., in a database 144) and/or utilized by a robot (e.g., a robot 130 and/or one or more robotic arms 132) for a surgery or surgical procedure.

As may be appreciated based on the foregoing disclosure, the present disclosure encompasses methods with fewer than all of the steps identified in FIG. 2 (and the corresponding description of the method 200), as well as methods that include additional steps beyond those identified in FIG. 2 (and the corresponding description of the method 200).

Figure 3:
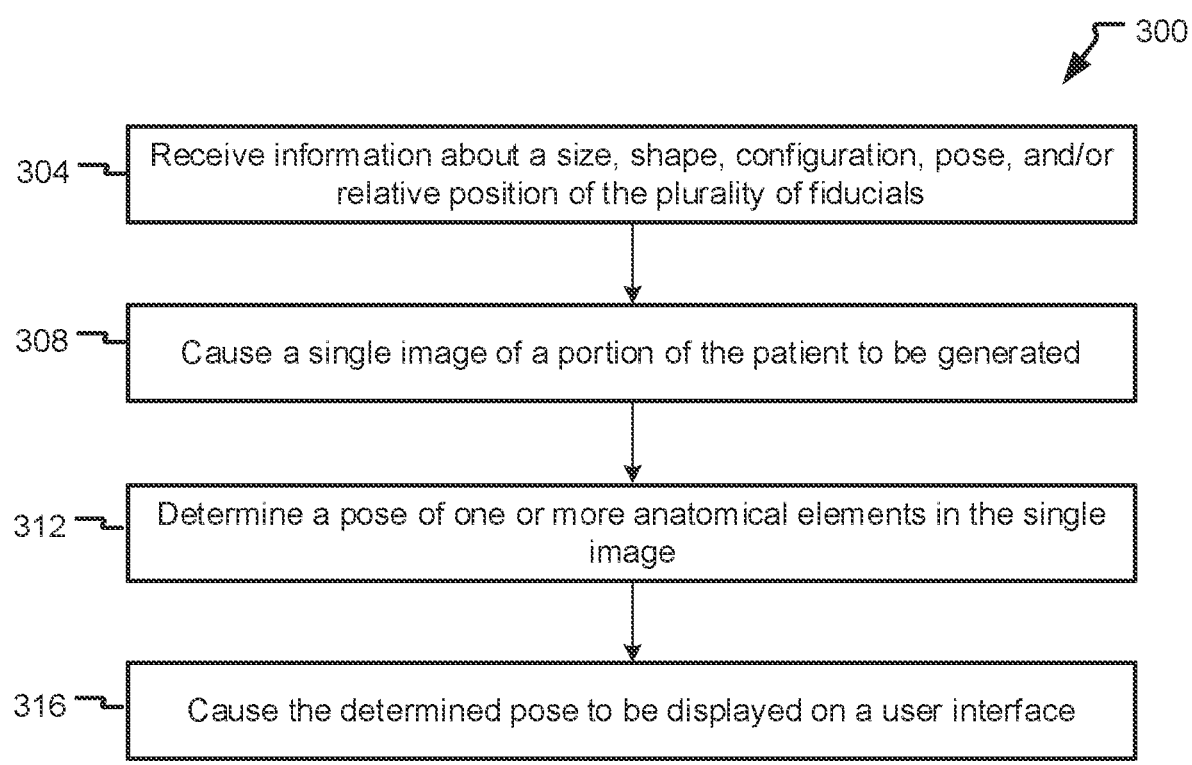
FIG. 3 is an additional flowchart of a method in accordance with embodiments of the present disclosure.

Turning to FIG. 3, a method 300 for displaying a determined pose to a user interface according to embodiments of the present disclosure is shown. The method 300 may be executed in part or in whole, for example, by a computing device 102 or similar device, and may utilize a system 100 and/or components thereof (e.g., a processor 104, one or more imaging devices 108, a navigation system 136, and/or combinations thereof, etc.). The at least one processor used to carry out the method 300 and/or one or more steps thereof may be the same as or similar to the processor(s) 104 of the computing device 102 described above. The at least one processor may be part of a robot (such as a robot 130 comprising one or more robotic arms 132), part of a navigation system (e.g., a navigation system 136), or part of a user interface (e.g., a user interface 112). A processor other than any processor described herein may also be used to execute the method 300. The at least one processor may perform the method 300 by executing instructions (such as the instructions 140) stored in a memory such as the memory 116. One or more aspects of the method 300 may be performed by or with a robot and/or surgical robotic arm (e.g., a robotic arm 132 attached to a robot 130) and/or components thereof. The method 300 may be used, for example, to update a registration (whether due to movement of a patient and/or one or more components of the system 100 during, for example, a surgery or surgical procedure, or otherwise). For instance, the patient may have shifted during surgery, and a new registration may be required to ensure surgical devices and/or instrumentation (e.g., a robot 130) is correctly positioned relative to the patient. The method 300 may additionally or alternatively be used to display a determined pose of one or more anatomical elements on a user interface, to be used by, for example, a surgeon during a surgery or surgical procedure.

The method 300 comprises receiving information about a size, shape, configuration, pose, and/or relative position of each of a plurality of fiducials (which are positioned on or within the patient) (step 304). The plurality of fiducials may be or comprise one or more screws, rods, intervertebral bodies, or other medical devices implanted into a patient. The information may be received via a user interface such as a user interface 112 and/or a communication interface (e.g., communication interface 106) and may be stored by a computing device (e.g., a computing device 102) in a memory (e.g., a memory 116). In some embodiments, the information may be received from one or more components of a system 100, such as from a database 144 and/or a cloud 148 and/or from external components of the system 100 (e.g., from other computing devices and/or databases). The information may comprise a CAD (computer-aided design) model of one or more of the plurality of fiducials. The information may correspond to a reflectivity of the one or more fiducials. The information may correspond to a surgical plan and/or to data from a robot used to execute a surgical plan, and may include, for example, information about a pose (e.g., a position and orientation), or a position or an orientation, of a given fiducial as inserted into the patient relative to the patient's anatomy. The information may comprise additional data about the plurality of fiducials (e.g., number of the fiducials inserted into the patient, relative time of placement of the plurality of fiducials, etc.) and/or the surgical procedure (e.g., type of surgical procedure, duration of surgical procedure, etc.). In some embodiments, the information may comprise a CT, MRI, or other preoperative image that depicts one or more of the plurality of fiducials.

The information received may depict at least a size, shape, configuration, pose, and/or relative position of the fiducials. The size of each of the plurality of fiducials may be or comprise the dimensions (e.g., length, width, height, etc.) of each fiducial. The shape of each of the plurality of fiducials may be information directed to an outline, geometric form, contours, surfaces, edges, and/or the like of the plurality of fiducials. The pose of each of the plurality of fiducials may be the location and orientation of each of the fiducials relative to the patient or in another specified coordinate space. The relative position of each fiducial may be a measurement of the relative distance of each fiducial from the remaining fiducials of the plurality of fiducials. The information may, in some embodiments, be input into one or more algorithms (e.g., a pose algorithm 122) to extract or determine additional information therefrom and/or to transform the information into information that is useful for the system (e.g., information useful for or relating to registration). In some embodiments, the information about the plurality of fiducials may be further stored/saved (e.g., in a database 144, a memory 116, or elsewhere) within the system 100.

The method 300 also comprises causing a single image of a portion of the patient to be generated (step 308). For instance, a computing device 102 (and more specifically, a processor 104) may cause an imaging device (e.g., an imaging device 108) to generate (e.g., capture) an image of a portion of the patient that comprises on or more of the plurality of fiducials. The single image may be, for example, a fluoroscopy image. In some embodiments, the processor may cause the imaging device to move into a first pose (e.g., position and orientation) relative to the patient, such that the imaging device can view every fiducial of the plurality of fiducials. In some embodiments, the first pose may be a position and orientation such that every fiducial of the plurality of fiducials is seen by the imaging device and such that relative spacing and depth information (e.g., where each fiducial is located in a coordinate system and how far away each fiducial is from the camera with respect to the coordinate system) of each of the plurality of fiducials may be determined from the captured image and the information received in the step 304. In some embodiments, only portions of each of the plurality of fiducials may be captured by the image. For instance, only a percentage of each of the plurality of fiducials (e.g., 1%, 2%, 5%, 10%, 15%, 25%, 50%, 75%, 80%, 90%, etc.) may be present in the image. In such embodiments, the percentage may be different for each of the plurality of fiducials. In some embodiments, the image may only depict a percentage of the total number of fiducials (e.g., only half of the total number of fiducials). In some embodiments, the method 300 causes only a single image of the portion of the patient to be generated. The imaging device may send the captured image to one or more components in the system 100 (e.g., to the computing device 102, the database 144, etc.) and/or to components outside the system 100. Each of the fiducials of the plurality of fiducials may be present in the image and may be distinguishable from other artifacts or structure in the image. For instance, in embodiments where the plurality of fiducials comprises screws, the imaging device 108 may emit radioactive waves (e.g., X-rays) with a detector positioned such that the plurality of fiducials is between the imaging device 108 and the detector. The resulting image may highlight (e.g., display in a different color, texture, intensity, and/or shape) the plurality of fiducials positioned within the patient. As previously noted, the plurality of fiducials may be attached or located proximate to one or more anatomical elements (e.g., internal organs, bones, ligaments, tendons, muscle structures, other soft tissues and/or hard tissues, etc.). In such embodiments, the capture of the image depicting the portion of the patient may also depict relative positions of the one or more anatomical elements to which the fiducials are attached or proximally located.

In some embodiments, one or more of the plurality of fiducials may be placed on or within the patient before a surgery or surgical procedure. For instance, one or more of the plurality of fiducials may be fixed to the skin of the patient (or even to the bony anatomy of the patient, whether via a small incision or otherwise) before a surgery begins. Also in some embodiments, one or more of the plurality of fiducials may have been previously implanted in a patient (e.g., during an initial surgery), permitting the system 100 to capture (e.g., via an imaging device 108) a relative layout of the plurality of fiducials prior to a subsequent surgery (e.g., a revision surgery). The system 100 may use the captured information intraoperatively, to compare the layout of the plurality of fiducials with a new image of the plurality of fiducials captured during or after the surgery or surgical procedure.

Also, as noted above, in some embodiments, the one or more of the plurality of fiducials may be implanted in the patient. For instance, the surgery or surgical procedure may be directed toward procedures performed within the patient. In such embodiments, one or more of the plurality of fiducials may be implanted in specific locations in the patient (e.g., anatomical features, structure, or the like). This may permit the system 100 and/or components thereof to determine the relative anatomical structure of the patient.

The plurality of fiducials may then be removed from the patient during and/or after the surgery or surgical procedure. The plurality of fiducials is in no way limiting, and examples may include screws, tracking devices, radio frequency identification (RFID) tags, or the like. The screws may be, for example, pedicle screws, cortical screws, cancellous screws, combinations thereof, and/or the like.

In some embodiments, the plurality of fiducials may be positioned such that a depth measurement may be obtained from the image. The depth measurement may be determined based on the viewing a first surface of a fiducial. For instance, the first surface of the fiducial may be angled relative to the first pose of the imaging device, such that the imaging device may only see an isometric (e.g., perspective) view of the fiducial. In other words, the fiducial is neither orthogonal (e.g., such that the imaging device views only a top or bottom of the fiducial without viewing a side) nor lateral (e.g., such that the imaging device views only a side of the fiducial without viewing the top or bottom). Rather, the view of the fiducial seen by the imaging device (and subsequently appearing in the image) may be such that the first surface is viewed in addition to at least one of the top, bottom, and side of the fiducial. The appearance of at least two surfaces may permit the method 300 to determine a depth of the fiducial (e.g., how far away each point of the fiducial is from the imaging device with respect to a coordinate system) using the information received in the step 304 and by determining an angle of the fiducial in the captured image.

The method 300 also comprises determining a pose of one or more anatomical elements in the single captured image (step 312). The determining may be based on the information received in the step 304 as well as the image generated in the step 308. The determining may use one or more algorithms such as a pose algorithm 122. The pose determination may include using coordinates for and/or an orientation of the plurality of fiducials attached to or near the one or more anatomical elements. In some embodiments, the pose algorithm may be configured to calculate the one or more poses based on the plurality of fiducials captured in the image and the information received in the step 304. For instance, the pose algorithm may determine that a fiducial is attached to or near an anatomical element, and may use the received information about the size, shape, configuration, pose, and/or relative position of the fiducial, together with the image generated in the step 308, to define a pose of the anatomical element. In some embodiments, the pose algorithm may output the defined pose relative to a predetermined coordinate system, a robot, and/or other components (e.g., other components of the system 100). In some embodiments, the pose algorithm may be or use artificial intelligence (AI), machine learning (e.g., deep learning), and/or other solutions to identify, detect, or otherwise recognize the fiducials. The determined pose may be sent to and/or stored in one or more components of the system 100. The method 300 may additionally or alternatively make use of an image processing algorithm (e.g., an image processing algorithm 120). The image processing algorithm may receive the captured image (e.g., from the imaging device) and may filter, process, or otherwise digitally manipulate the single image. Such post-image processing may improve storage efficiency of the image and/or may improve the image quality to more easily facilitate the pose determination (e.g., by improving the quality of the image passed to the pose algorithm).

In some embodiments, the depth of each of the plurality of fiducials may be determined. In embodiments where the imaging device captures a view of at least two surfaces of the fiducial, the relative depth may be determined through an angle measurement together with the information received in the step 304. For instance, the pose algorithm may determine a relative angle of the fiducial in the image of the portion of the patient and may calculate the pose of the fiducial using the angle and position information (e.g., information received about the relative position of the fiducials). A first surface of each fiducial may be the surface from which the pose algorithm measures the relative angle. The selection of the first surface is not limited, and the choice of the first surface may be arbitrary and may additionally or alternatively be selected based on the appearance of the fiducial in the image, based on predetermined instructions for the designation of the first surface, and/or the like. The angle of the first surface may appear in the single image at an angle of greater than 0 degrees and less than 90 degrees, greater than 10 degrees and less than 80 degrees, greater than 20 degrees and less than 70 degrees, etc. It is to be understood, however, that the above degree ranges are in no way limiting to the embodiments of the present disclosure, and additional or alternative angle ranges of between 0 and 90 degrees are possible. The method 300 may use the determined fiducial location to further determine the pose of one or more anatomical elements. For instance, in embodiments where the plurality of fiducials have been affixed to one or more anatomical elements, the pose of the fiducial may allow the processor to determine the relative pose of the one or more anatomical elements. In some embodiments, one or more of the plurality of fiducials may be attached on or near the one or more anatomical elements, which may allow for the determination of the pose of the one or more anatomical elements based on the relative poses of the plurality of fiducials and the known distances between the plurality of fiducials and the one or more anatomical elements. In some embodiments, the pose of one or more anatomical elements is compared to a target pose. For instance, the target pose may be a predicted or expected pose of each of the one or more anatomical elements. The comparison algorithm may compare the determined pose against the target pose to determine a level of accuracy (e.g., how closely the determined pose is to a desired pose). In some embodiments, the method may include sending a warning to a user interface (e.g., a user interface 112) when the determined pose is outside a threshold accuracy level from the target pose.

The method 300 also comprises causing the determined pose to be displayed on a user interface (step 316). The user interface (such as user interface 112) may allow a surgeon to view the pose determined based on the single image and the received information. The determined pose of the one or more anatomical elements may be referenced by a surgeon or technician for the purposes of reviewing the accuracy of the determined pose, to assist in the performance of a surgical procedure, and/or to determine if an updated registration is required for the surgery or surgical procedure. In some embodiments, the method 300 may cause the user interface to render the single image and/or the determined pose of the one or more anatomical elements. In some embodiments, the determined pose may be rendered as metadata and/or as an image depicting the determined pose. The display may be used by the surgeon to adjust or verify the surgery or surgical operation.

The rendering of the determined pose may display the one or more anatomical elements with different visual indicia based on the type of tissue (e.g., soft tissue or hard tissue), based on relative movement of the one or more anatomical elements when compared to a baseline pose value (e.g., based on a predetermined pose), combinations thereof, and/or the like. For example, sensitive anatomical elements that have moved out of position between the calculation of the predetermined pose and the calculation of the determined pose may be displayed more prominently (e.g., greater intensity, contrast, etc.) than anatomical elements that have moved less (e.g., below a predetermined threshold value). In some embodiments, the determined pose may be displayed with metadata associated with each of the one or more anatomical elements, which may assist the surgeon to distinguish the one or more anatomical elements and thus to better view the pose of the one or more anatomical elements on the user interface. In some embodiments, the determined pose may be overlayed on the predetermined pose of the one or more anatomical elements. The overlay may permit a user (e.g., a surgeon) to better determine visually the difference in pose of the determined pose relative to the predetermined pose. Information about an amount or degree by which a determined pose of one or more anatomical elements differs from a predetermined pose of the one or more anatomical elements (whether in absolute or relative terms) may also be displayed.

As may be appreciated based on the foregoing disclosure, the present disclosure encompasses methods with fewer than all of the steps identified in FIG. 3 (and the corresponding description of the method 300), as well as methods that include additional steps beyond those identified in FIG. 3 (and the corresponding description of the method 300).

Figure 4:
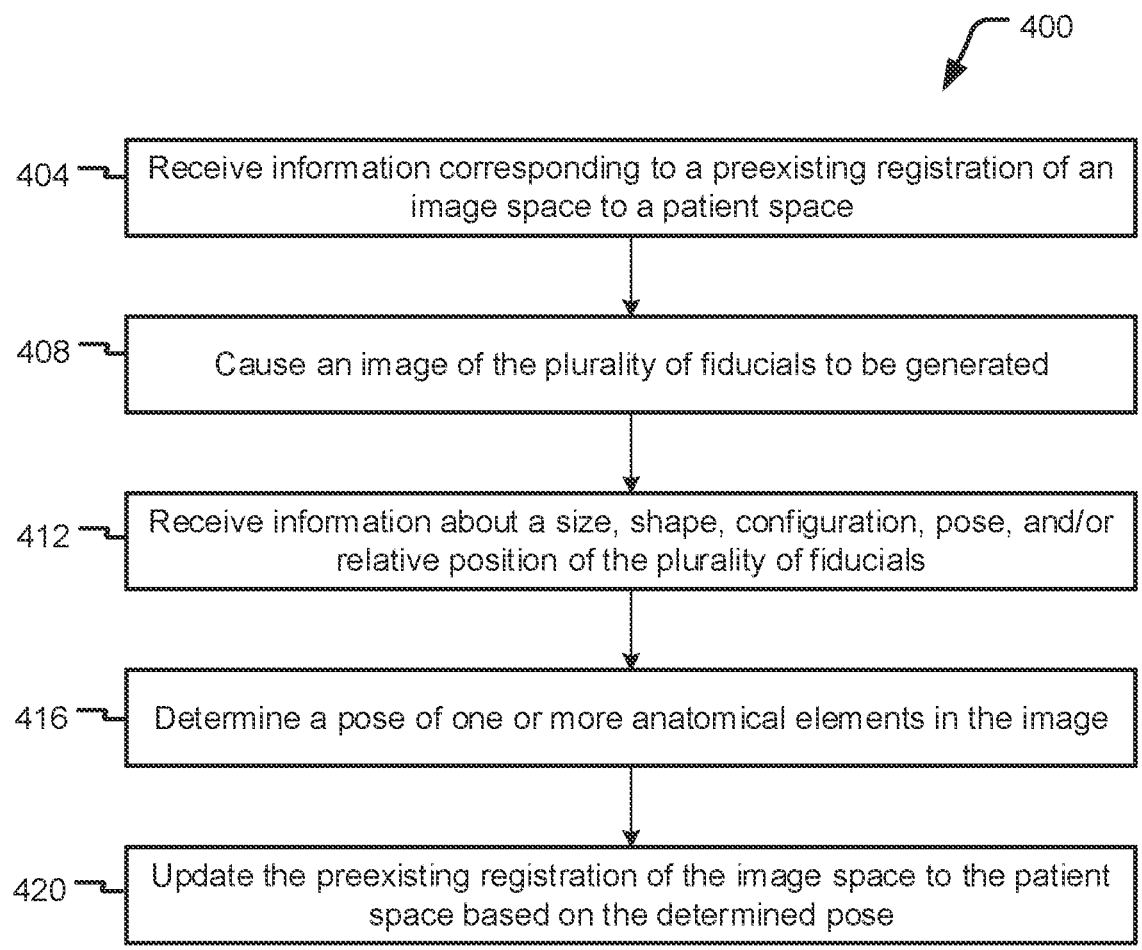
FIG. 4 is another flowchart of a method in accordance with embodiments of the present disclosure.

Turning to FIG. 4, a method 400 for updating a registration according to embodiments of the present disclosure is shown. The method 400 may be executed in part or in whole, for example, by a computing device 102 or similar device, and may utilize a system 100 and/or components thereof (e.g., a processor 104, one or more imaging devices 108, a navigation system 136, and/or combinations thereof, etc.). The at least one processor used to carry out the method 400 and/or one or more steps thereof may be the same as or similar to the processor(s) 104 of the computing device 102 described above. The at least one processor may be part of a robot (such as a robot 130 comprising one or more robotic arms 132), part of a navigation system (e.g., a navigation system 136), or part of a user interface (e.g., a user interface 112). A processor other than any processor described herein may also be used to execute the method 400. The at least one processor may perform the method 400 by executing instructions (such as the instructions 140) stored in a memory such as the memory 116. One or more aspects of the method 400 may be performed by or with a robot and/or surgical robotic arm (e.g., a robotic arm 132 attached to a robot 130) and/or components thereof. The method 400 may be used, for example, to update a registration based on movement of a patient and/or one or more components of the system 100 during, for example, a surgery or surgical procedure. For instance, the patient may have shifted during surgery, and a new registration may be required to ensure surgical devices and/or instrumentation (e.g., a robot 130) are correctly positioned relative to the patient. The method 400 may additionally or alternatively be used to display a determined pose of one or more anatomical elements on a user interface to be used by, for example, a surgeon during a surgery or surgical procedure.

The method 400 also comprises receiving information corresponding to a preexisting registration of an image space to a patient space (step 404). The information may comprise, for example, a CT image, an MRI image, or another preoperative image of the patient, and/or one or more intraoperative images of the patient. Any such images may be taken with an imaging device such as the imaging device 108 or any other imaging device. The information may additionally or alternatively comprise a function or algorithm for translating coordinates in one of an image space and a patient space to the other of the image space and the patient space. The information may comprise information about a pose (at the time of the preexisting registration) of one or more fiducials and/or one or more anatomical elements.

The method 400 also comprises causing a single image of a portion of the patient to be generated (step 408). For instance, a computing device 102 (and more specifically, a processor 104) may cause an imaging device (e.g., an imaging device 108) to generate (e.g., capture) an image of a portion of the patient that comprises on or more of the plurality of fiducials. The single image may be, for example, a fluoroscopy image. In some embodiments, the processor may cause the imaging device to move into a first pose (e.g., position and orientation) relative to the patient, such that the imaging device can view every fiducial of the plurality of fiducials. In some embodiments, the first pose may be a position and orientation such that every fiducial of the plurality of fiducials is seen by the imaging device and such that relative spacing and depth information (e.g., where each fiducial is located in a coordinate system and how far away each fiducial is from the camera with respect to the coordinate system) of each of the plurality of fiducials may be determined from the captured image and the information received in the step 404. In some embodiments, only portions of each of the plurality of fiducials may be captured by the image. For instance, only a percentage of each of the plurality of fiducials (e.g., 1%, 2%, 5%, 10%, 15%, 25%, 50%, 75%, 80%, 90%, etc.) may be present in the image. In such embodiments, the percentage may be different for each of the plurality of fiducials. In some embodiments, the image may only depict a percentage of the total number of fiducials (e.g., only half of the total number of fiducials). In some embodiments, the method 400 causes only a single image of the portion of the patient to be generated. The imaging device may send the captured image to one or more components in the system 100 (e.g., to the computing device 102, the database 144, etc.) and/or to components outside the system 100. Each of the fiducials of the plurality of fiducials may be present in the image and may be distinguishable from other artifacts or structure in the image. For instance, in embodiments where the plurality of fiducials comprises screws, the imaging device 108 may emit radioactive waves (e.g., X-rays) with a detector positioned such that the plurality of fiducials is between the imaging device 108 and the detector. The resulting image may highlight (e.g., display in a different color, texture, intensity, and/or shape) the plurality of fiducials positioned within the patient. As previously noted, the plurality of fiducials may be attached or located proximate to one or more anatomical elements (e.g., internal organs, bones, ligaments, tendons, muscle structures, other soft tissues and/or hard tissues, etc.). In such embodiments, the capture of the image depicting the portion of the patient may also depict relative positions of the one or more anatomical elements to which the fiducials are attached or proximally located.

In some embodiments, one or more of the plurality of fiducials may be placed on or within the patient before a surgery or surgical procedure. For instance, one or more of the plurality of fiducials may be fixed to the skin of the patient (or even to the bony anatomy of the patient, whether via a small incision or otherwise) before a surgery begins. Also in some embodiments, one or more of the plurality of fiducials may have been previously implanted in a patient (e.g., during an initial surgery), permitting the system 100 to capture (e.g., via an imaging device 108) a relative layout of the plurality of fiducials prior to a subsequent surgery (e.g., a revision surgery). The system 100 may use the captured information intraoperatively, to compare the layout of the plurality of fiducials with a new image of the plurality of fiducials captured during or after the surgery or surgical procedure.

Also, as noted above, in some embodiments, the one or more of the plurality of fiducials may be implanted in the patient. For instance, the surgery or surgical procedure may be directed toward procedures performed within the patient. In such embodiments, one or more of the plurality of fiducials may be implanted in specific locations in the patient (e.g., anatomical features, structure, or the like). This may permit the system 100 and/or components thereof to determine the relative anatomical structure of the patient. The plurality of fiducials may then be removed from the patient during and/or after the surgery or surgical procedure. The plurality of fiducials is in no way limiting, and examples may include screws, tracking devices, radio frequency identification (RFID) tags, or the like. The screws may be, for example, pedicle screws, cortical screws, cancellous screws, combinations thereof, and/or the like.

In some embodiments, the plurality of fiducials may be positioned such that a depth measurement may be obtained from the image. The depth measurement may be determined based on the viewing a first surface of a fiducial. For instance, the first surface of the fiducial may be angled relative to the first pose of the imaging device, such that the imaging device may only see an isometric (e.g., perspective) view of the fiducial. In other words, the fiducial is neither orthogonal (e.g., such that the imaging device views only a top or bottom of the fiducial without viewing a side) nor lateral (e.g., such that the imaging device views only a side of the fiducial without viewing the top or bottom). Rather, the view of the fiducial seen by the imaging device (and subsequently appearing in the image) may be such that the first surface is viewed in addition to at least one of the top, bottom, and side of the fiducial. The appearance of at least two surfaces may permit the method 400 to determine a depth of the fiducial (e.g., how far away each point of the fiducial is from the imaging device with respect to a coordinate system) using the information received in the step 404 and by determining an angle of the fiducial in the captured image.

The method 400 comprises receiving information about a size, shape, configuration, pose, and/or relative position of each of a plurality of fiducials (which are positioned on or within the patient) (step 412). The plurality of fiducials may be or comprise one or more screws, rods, intervertebral bodies, or other medical devices implanted into a patient. The information may be received via a user interface such as a user interface 112 and/or a communication interface (e.g., communication interface 106) and may be stored by a computing device (e.g., a computing device 102) in a memory (e.g., a memory 116). In some embodiments, the information may be received from one or more components of a system 100, such as from a database 144 and/or a cloud 148 and/or from external components of the system 100 (e.g., from other computing devices and/or databases). The information may comprise a CAD (computer-aided design) model of one or more of the plurality of fiducials. The information may correspond to a reflectivity of the one or more fiducials. The information may correspond to a surgical plan and/or to data from a robot used to execute a surgical plan, and may include, for example, information about a pose (e.g., a position and orientation), or a position or an orientation, of a given fiducial as inserted into the patient relative to the patient's anatomy. The information may comprise additional data about the plurality of fiducials (e.g., number of the fiducials inserted into the patient, relative time of placement of the plurality of fiducials, etc.) and/or the surgical procedure (e.g., type of surgical procedure, duration of surgical procedure, etc.). In some embodiments, the information may comprise a CT image, an MRI image, or another image that depicts the plurality of fiducials.

The information received may depict at least a size, shape, configuration, pose, and/or relative position of the fiducials. The size of each of the plurality of fiducials may be or comprise the dimensions (e.g., length, width, height, etc.) of each fiducial. The shape of each of the plurality of fiducials may be information directed to an outline, geometric form, contours, surfaces, edges, and/or the like of the plurality of fiducials. The pose of each of the plurality of fiducials may be the location and orientation of each of the fiducials relative to the patient or in another specified coordinate space. The relative position of each fiducial may be a measurement of the relative distance of each fiducial from the remaining fiducials of the plurality of fiducials. The information may, in some embodiments, be input into one or more algorithms (e.g., a pose algorithm 122) to extract or determine additional information therefrom and/or to transform the information into information that is useful for the system (e.g., information useful for or relating to registration). In some embodiments, the information about the plurality of fiducials may be further stored/saved (e.g., in a database 144, a memory 116, or elsewhere) within the system 100.

The method 400 also comprises determining a pose of one or more anatomical elements in the single captured image (step 416). The determining may be based on the information received in the steps 404 and/or 412 as well as the image generated in the step 408. The determining may use one or more algorithms such as a pose algorithm 122. The pose determination may include using coordinates for and/or an orientation of the plurality of fiducials attached to or near the one or more anatomical elements. In some embodiments, the pose algorithm may be configured to calculate the one or more poses based on the plurality of fiducials captured in the image and the information received in the step 412. For instance, the pose algorithm may determine that a fiducial is attached to or near an anatomical element, and may use the received information about the size, shape, configuration, pose, and/or relative position of the fiducial, together with the image generated in the step 308, to define a pose of the anatomical element. In some embodiments, the pose algorithm may output the defined pose relative to a predetermined coordinate system, a robot, and/or other components (e.g., other components of the system 100). In some embodiments, the pose algorithm may be or use artificial intelligence (AI), machine learning (e.g., deep learning), and/or other solutions to identify, detect, or otherwise recognize the fiducials. The determined pose may be sent to and/or stored in one or more components of the system 100. The method 400 may additionally or alternatively make use of an image processing algorithm (e.g., an image processing algorithm 120). The image processing algorithm may receive the captured image (e.g., from the imaging device) and may filter, process, or otherwise digitally manipulate the single image. Such post-image processing may improve storage efficiency of the image and/or may improve the image quality to more easily facilitate the pose determination (e.g., by improving the quality of the image passed to the pose algorithm).

In some embodiments, the depth of each of the plurality of fiducials may be determined. In embodiments where the imaging device captures a view of at least two surfaces of the fiducial, the relative depth may be determined through an angle measurement together with the information received in the step 412. For instance, the pose algorithm may determine a relative angle of the fiducial in the image of the portion of the patient and may calculate the pose of the fiducial using the angle and position information (e.g., information received about the relative position of the fiducials). A first surface of each fiducial may be the surface from which the pose algorithm measures the relative angle. The selection of the first surface is not limited, and the choice of the first surface may be arbitrary and may additionally or alternatively be selected based on the appearance of the fiducial in the image, based on predetermined instructions for the designation of the first surface, and/or the like. The angle of the first surface may appear in the single image at an angle of greater than 0 degrees and less than 90 degrees, greater than 10 degrees and less than 80 degrees, greater than 20 degrees and less than 70 degrees, etc. It is to be understood, however, that the above degree ranges are in no way limiting to the embodiments of the present disclosure, and additional or alternative angle ranges of between 0 and 90 degrees are possible. The method 300 may use the determined fiducial location to further determine the pose of one or more anatomical elements. For instance, in embodiments where the plurality of fiducials have been affixed to one or more anatomical elements, the pose of the fiducial may allow the processor to determine the relative pose of the one or more anatomical elements. In some embodiments, one or more of the plurality of fiducials may be attached on or near the one or more anatomical elements, which may allow for the determination of the pose of the one or more anatomical elements based on the relative poses of the plurality of fiducials and the known distances between the plurality of fiducials and the one or more anatomical elements. In some embodiments, the pose of one or more anatomical elements is compared to a target pose. For instance, the target pose may be a predicted or expected pose of each of the one or more anatomical elements. The comparison algorithm may compare the determined pose against the target pose to determine a level of accuracy (e.g., how closely the determined pose is to a desired pose). In some embodiments, the method may include sending a warning to a user interface (e.g., a user interface 112) when the determined pose is outside a threshold accuracy level from the target pose.

The method 400 also comprises updating the preexisting registration of the image space to the patient space based on the determined pose of one or more anatomical elements (step 420). The method 400 may make use of one or more algorithms (e.g., a registration update or comparison algorithm 128). The one or more algorithms may compare the determined pose of the one or more anatomical elements against a predetermined pose of the one or more anatomical elements. For instance, the one or more algorithms may receive the determined pose of the one or more anatomical elements and compare the determined pose to a predetermined pose. In such embodiments, the one or more algorithms may determine that the determined pose and the predetermined pose do not match in value and/or are outside of a tolerance value. As a result, the one or more algorithms may update the registration of the image space to the patient space. The updating of the registration may map the determined pose to the patient space (e.g., using the location and orientation information associated with the determined pose), and may update a surgical plan (e.g., a surgical plan 134) to reflect the changed pose of the one or more anatomical elements relative to the patient space. In some embodiments, the system and/or components thereof (e.g., a robot 130 and/or one or more robotic arms 132) may then be autonomously or semi-autonomously operated based on the updated registration. In some embodiments, the updating of the registration may comprise deleting the previous registration or replacing the previous registration with a new registration.

The new registration may be at least partially based on the received information and the determined pose of the one or more anatomical elements in the image. For instance, the information about the plurality of fiducials (as well as the image of the plurality of fiducials) may facilitate updating the registration with acceptable accuracy despite only one image of the plurality of fiducials being generated. The one or more algorithms may output an updated registration, which may be passed to one or more of a robot (e.g., a robot 130 and/or one or more robotic arms 132), a surgical plan (e.g., a surgical plan 134), and/or a database (e.g., a database 144). In some embodiments, the updated registration may then be used by one or more components of a system (e.g., a system 100) to perform a surgery or surgical procedure with the new registration.

As may be appreciated based on the foregoing disclosure, the present disclosure encompasses methods with fewer than all of the steps identified in FIG. 4 (and the corresponding description of the method 400), as well as methods that include additional steps beyond those identified in FIG. 4 (and the corresponding description of the method 400).

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method, comprising:
receiving information about a three-dimensional (3D) shape and a 3D pose of each of a plurality of fiducials positioned on or within a patient;
causing an imaging device to generate a single image of a portion of the patient, the single image depicting at least a surface and an edge of each of the plurality of fiducials and one or more anatomical elements;
identifying the surface and the edge of each of the plurality of fiducials, wherein the identifying comprises determining a depth of each of the plurality of fiducials depicted in the single image and determining an angle of each of the plurality of fiducials depicted in the single image relative to the imaging device;
determining, based on the information about the 3D shape and the 3D pose and the single image, a pose of the one or more anatomical elements represented in the single image;
comparing the determined pose of the one or more anatomical elements to a predetermined pose of the one or more anatomical elements;
quantifying a difference between the determined pose of the one more anatomical elements and the predetermined pose of the one or more anatomical elements, wherein the respective difference is a percentage of the determined pose of each of the one more anatomical elements that matches the predetermined pose of each of the one or more anatomical elements;
updating a preexisting registration using the determined pose; and
navigating a robot based on the updated registration.

2. The method of claim 1, wherein comparing the determined pose further comprises comparing the determined pose to a target pose of the one or more anatomical elements in a surgical plan.

3. The method of claim 1, further comprising:
determining a position of the imaging device relative to the plurality of fiducials based on use of a phantom.

4. The method of claim 1, wherein the plurality of fiducials comprises one or more screws.

5. The method of claim 1, wherein the plurality of fiducials comprises a plurality of different types of implants.

6. The method of claim 1, wherein the single image further depicts a device held by the robot, and wherein the method further comprises:
locating the determined pose in a coordinate space corresponding to the robot based on the single image.

7. The method of claim 1, wherein the information comprises a Computer Aided Design (CAD) model of at least one of the plurality of fiducials.

8. A system, comprising:
a processor; and
a memory storing instructions for execution by the processor that, when executed by the processor, enable the processor to:
receive information about a three-dimensional (3D) shape and a 3D pose of a plurality of tracking devices disposed on or within a patient;
cause an imaging device to generate a single image of a portion of the patient, the single image depicting at least a surface and an edge of each of the plurality of tracking devices and one or more anatomical elements;
identify the surface and the edge of each of the plurality of tracking devices in the single image, wherein the identifying comprises determining a depth of each of the plurality of tracking devices depicted in the single image, and wherein the identifying further comprises determining an angle of each of the plurality of tracking devices depicted in the single image relative to the imaging device;
calculate, based on the information and the surface and the edge of each of the plurality of tracking devices identified in the single image, a pose of the one or more anatomical elements represented in the single image;
compare the calculated pose of the one or more anatomical elements to a predetermined pose of the one or more anatomical elements;
quantify a respective difference between the calculated pose of each of the one more anatomical elements and the predetermined pose of each of the one or more anatomical elements, wherein the respective difference is a percentage of the calculated pose of each of the one more anatomical elements that matches the predetermined pose of each of the one or more anatomical elements;
update a preexisting registration using the calculated pose; and
navigate a robot based on the updated registration.

9. The system of claim 8, wherein the imaging device is fixed in a first pose relative to the patient.

10. The system of claim 9, wherein a first surface of each of the surfaces of the plurality of tracking devices in the single image appears at an angle greater than ten degrees and less than eighty degrees relative to the imaging device.

11. The system of claim 8, wherein the single image is generated using fluoroscopy.

12. The system of claim 8, wherein the plurality of tracking devices comprises a plurality of different types of implants.

13. The system of claim 8, wherein at least one of the plurality of tracking devices is a screw implanted in the patient.

14. The system of claim 8, wherein the plurality of tracking devices comprises one or more screws.

15. The system of claim 8, wherein each of the one or more anatomical elements is a vertebra.

16. A system, comprising:
a processor;
an imaging device;
a plurality of fiducials disposed on or within a patient; and
a memory storing instructions for execution by the processor that, when executed by the processor, enable the processor to:
receive information about a three-dimensional (3D) shape and a 3D pose of the plurality of fiducials;
cause the imaging device to generate an image of a portion of the patient, the image comprising the plurality of fiducials and one or more anatomical tissues;
identify at least a surface and an edge of each of the plurality of fiducials depicted in the image;
determine, based on the image and the surface and the edge of each of the plurality of fiducials identified in the image, a depth of each of the plurality of fiducials and an angle of each of the plurality of fiducials depicted in the image relative to the imaging device;
determine, based on the information and the image, a pose of the one or more anatomical tissues represented in the image;
cause the determined pose of the one or more anatomical tissues to be displayed on a user interface;

quantifying a difference between the determined pose of the one more anatomical elements and a predetermined pose of the one or more anatomical tissues, wherein the difference is a percentage of the determined pose of each of the one more anatomical tissues that matches the predetermined pose of each of the one or more anatomical tissues;

update a preexisting registration using the determined pose; and navigate a robot based on the updated registration.

17. The system of claim 16, wherein the determined pose of the one or more anatomical tissues is displayed on the user interface as an overlay on a target pose of the one or more anatomical tissues.

* * * * *